United States Patent
Masterson et al.

(10) Patent No.: US 7,787,728 B2
(45) Date of Patent: Aug. 31, 2010

(54) OPTICAL MODE NOISE AVERAGING DEVICE

(75) Inventors: Bernard Patrick Masterson, Boulder, CO (US); Eric C. Huelson, Golden, CO (US); Ian S. Smith, Boulder, CO (US)

(73) Assignee: Zolo Technologies, Inc., Boulder, CO (US)

( * ) Notice: Subject to any disclaimer, the term of this patent is extended or adjusted under 35 U.S.C. 154(b) by 395 days.

(21) Appl. No.: 10/599,233

(22) PCT Filed: Feb. 2, 2005

(86) PCT No.: PCT/US2005/002853

§ 371 (c)(1),
(2), (4) Date: Nov. 27, 2006

(87) PCT Pub. No.: WO2005/103781

PCT Pub. Date: Nov. 3, 2005

(65) Prior Publication Data

US 2008/0002186 A1    Jan. 3, 2008

(51) Int. Cl.
G02B 6/02    (2006.01)
(52) U.S. Cl. ........................ 385/123; 356/73.1
(58) Field of Classification Search ............... 385/12, 385/13, 123; 356/73.1
See application file for complete search history.

(56) References Cited

U.S. PATENT DOCUMENTS

| | | | |
|---|---|---|---|
| 4,011,403 A | 3/1977 | Epstein et al. | |
| 4,028,081 A | 6/1977 | Marcatili | |
| 4,305,640 A | 12/1981 | Cullis et al. | |
| 4,360,372 A | 11/1982 | Maciejko | |
| 4,672,198 A * | 6/1987 | Presby ............... | 356/73.1 |
| 4,895,421 A | 1/1990 | Kim et al. | |
| 4,915,468 A | 4/1990 | Kim et al. | |
| 4,989,979 A | 2/1991 | Buckman | |
| 5,042,905 A | 8/1991 | Anjan et al. | |

(Continued)

FOREIGN PATENT DOCUMENTS

CN    1163665 A    10/1997

(Continued)

OTHER PUBLICATIONS

Allen (1998) "Diode laser absorption sensors for gas-dynamic and combustion flows" Measuring Science and Technology 9:545.

(Continued)

*Primary Examiner*—Ellen Kim
(74) *Attorney, Agent, or Firm*—Swanson & Bratschun, L.L.C.

(57) ABSTRACT

An optical mode noise averaging device including a multimode optical fiber and means for averaging a modal noise induced signal level variation of light propagating within the multimode optical fiber. The device may average modal noise induced signal level variations by cyclically varying an index of refraction of the multimode optical fiber over a select period of time, scrambling a light distribution within the multimode optical fiber, or both. The index of refraction of the multimode optical fiber may be cyclically varied by cyclically varying the temperature of the multimode optical fiber. Alternatively, the index for refraction may be varied or the light distribution within the multimode optical fiber may be scrambled by cyclically manipulating the multimode optical fiber.

14 Claims, 7 Drawing Sheets

U.S. PATENT DOCUMENTS

| | | | |
|---|---|---|---|
| 5,068,515 A | | 11/1991 | van den Bergh et al. |
| 5,291,013 A | * | 3/1994 | Nafarrate et al. ........ 250/227.14 |
| 5,396,506 A | | 3/1995 | Ball |
| 5,436,444 A | * | 7/1995 | Rawson ................. 250/227.14 |
| 5,448,071 A | | 9/1995 | McCaul et al. |
| 5,468,239 A | * | 11/1995 | Tanner et al. ................... 606/15 |
| 5,477,323 A | | 12/1995 | Andrews et al. |
| 5,506,721 A | | 4/1996 | Hikami et al. |
| 5,553,179 A | | 9/1996 | Cryan et al. |
| 5,598,264 A | * | 1/1997 | Failes .......................... 356/506 |
| 5,621,213 A | | 4/1997 | Barshad |
| 5,701,376 A | | 12/1997 | Shirasaki |
| 5,742,715 A | * | 4/1998 | Boehlke et al. ................ 385/32 |
| 5,798,840 A | | 8/1998 | Beiting |
| 5,802,222 A | | 9/1998 | Rasch et al. |
| 5,805,318 A | * | 9/1998 | Rabinovich et al. ........... 398/28 |
| 5,813,767 A | | 9/1998 | Calabro et al. |
| 5,841,915 A | * | 11/1998 | Rabinovich et al. ........... 385/13 |
| 5,933,000 A | | 8/1999 | Bosselmann et al. |
| 5,960,129 A | | 9/1999 | Kleinschmitt |
| 6,016,372 A | | 1/2000 | Fein et al. |
| 6,018,413 A | | 1/2000 | Oka |
| 6,148,131 A | | 11/2000 | Geertman |
| 6,150,661 A | | 11/2000 | McCaul et al. |
| 6,160,255 A | | 12/2000 | Sausa |
| 6,169,830 B1 | | 1/2001 | Kewitsch et al. |
| 6,345,134 B1 | | 2/2002 | Laming et al. |
| 6,351,587 B1 | | 2/2002 | Holland |
| 6,363,190 B1 | | 3/2002 | Chen |
| 6,385,372 B1 | | 5/2002 | Yang |
| 6,434,302 B1 | | 8/2002 | Fidric et al. |
| 6,455,851 B1 | | 9/2002 | Lord et al. |
| 6,510,265 B1 | * | 1/2003 | Giaretta et al. ................. 385/38 |
| 6,519,385 B1 | | 2/2003 | Green |
| 6,542,679 B2 | | 4/2003 | DiGiovanni et al. |
| 6,593,573 B1 | | 7/2003 | McCann et al. |
| 6,678,451 B2 | * | 1/2004 | Kim et al. .................... 385/124 |
| 6,701,753 B2 | * | 3/2004 | Dong et al. .................... 65/412 |
| 6,766,070 B2 | | 7/2004 | Williams et al. |
| 6,791,689 B1 | | 9/2004 | Weckstrom |
| 7,158,552 B2 | * | 1/2007 | Buchold et al. .......... 372/38.08 |
| 7,248,755 B2 | | 7/2007 | Sappey et al. |
| 2002/0031737 A1 | | 3/2002 | Von Drasek et al. |
| 2002/0158202 A1 | | 10/2002 | Webber et al. |
| 2002/0181856 A1 | | 12/2002 | Sappey et al. |
| 2003/0067952 A1 | * | 4/2003 | Tsukiji et al. .................. 372/36 |
| 2003/0101774 A1 | * | 6/2003 | Oh et al. ....................... 65/488 |
| 2003/0191397 A1 | | 10/2003 | Webb |
| 2004/0160596 A1 | * | 8/2004 | He et al. ..................... 356/73.1 |
| 2006/0147166 A1 | * | 7/2006 | Roba et al. .................. 385/123 |
| 2006/0278240 A1 | | 12/2006 | Spillman et al. |
| 2007/0217744 A1 | * | 9/2007 | Debut et al. .................... 385/50 |
| 2009/0080054 A1 | | 3/2009 | Koyata et al. |

FOREIGN PATENT DOCUMENTS

| | | |
|---|---|---|
| CN | 1343873 | 4/2002 |
| EP | 766080 | 4/1997 |
| JP | 63-133035 | 6/1988 |
| JP | 4-251214 | 9/1992 |
| JP | 07-504828 | 6/1995 |
| JP | 10-301153 | 11/1998 |
| JP | 2000-074830 | 3/2000 |
| JP | 2001-215343 | 8/2001 |
| JP | 2003-084324 | 3/2003 |
| JP | 2006-522938 | 10/2006 |

OTHER PUBLICATIONS

Allen et al. (2002) "Tunable Diode Laser Sensing and Combustion Control" Applied Combustion Diagnostics, chapter 18.

Baer et al. (1994) "Multiplexed Diode-Laser Sensor System for Simultaneous H20, 02, and Temperature Measurements" Optics Letters 19(22): 1900-1902.

Ebert et al. (1998) "Simultaneous Laser-Based in situ Detection of Oxygen and Water in a Waste Incinerator for Active Combustion Control Purposes" 27th Symposium on Combustion pp. 1301-1308.

Ebert et al. (2000) "Simultaneous Diode-Laser-Based In Situ Detection of Multiple Species and Temperature in a Gas-Fired Power Plant" Proceedings of the Combustion Institute 28:423.

Ebert et al. (2000) "The Use of Lasers as the Basis for Combustion Equipment Control" at TOTem, Intelligent Combustion Control pp. 1-15.

Furlong et al. (1998) "Diode Laser Sensors for Real-Time Control of Pulsed Combustion Systems": AIAA/SAE/ASME/ASEE Joint Propulsion Conference and Exhibit, pp. 1-8, 1, XP001148178.

Furlong et al. (1998) "Real-Time Adaptive Combustion Control Using Diode-Laser Absorption Sensors," 27th Symposium on Combustion pp. 103-111.

Liu et al. (2003) "Diode Laser Absorption Diagnostics for Measurements in Practical Combustion Flow Fields" 39th AIAA/ASME/SAE/ASEE Joint Propulsion Conference and Exhibit, Paper No. AIAA-2003-4581 pp. 1-6.

Miller et al. (1996) "Diode laser-based air mass flux sensor for subsonic aeropropulsion inlets" Applied Optics 35:4905.

Ouyang et al. (1992) "Tomographic Absorption Spectroscopy of Combustion Gases using Tunable Infrared Diode Lasers," Paper No. 1637-20, SPIE Conference on Environmental and Process Monitoring Technologies, pp. 163-172.

Phillippe et al. (1993) "Laser diode wavelength-modulation spectroscopy for simultaneous measurement of temperature, pressure, and velocity in shock-heated oxygen flows" Applied Optics 32:6090.

Sanders et al. (2000) "Diode-Laser Sensor for Monitoring Multiple Combustion Parameters in Pulse Detonation Engines" Proceedings of the Combustion Institute 28:587.

Sanders et al. (2001) "Diode-laser absorption sensor for line-of-sight gas temperature distributions" Applied Optics 40:4404.

Teichert et al. (2003) "Simultaneous in situ measurement of CO $H_2O$, and gas temperatures in a full-sized coal-fired power plant by near-infrared diode lasers" Applied Optics 42:2043.

Upschulte et al. (1999) "Measurements of CO, $CO_2$, OH, and $H_2O$ in room-temperature and combustion gases by use of a broadly current-tuned multisection InGaAsP diode laser" Applied Optics 38:1506.

Varghese et al. (1997) "Temperature and CO2 Concentration Profiles in Flames Measured by Laser Absorption Tomography," Paper 97-0317, AIAA 35th Aerospace Sciences Meeting, Reno, NV.

Villarreal et al. (2005) "Frequency Resolved Absorption Tomography with Tunable Diode Lasers," Applied Optics 44:6786-6795.

Webber et al. (2000) "In Situ Combustion Measurements of CO, $CO_2$, $H_2O$ and Temperature Using Diode Laser Absorption Sensors" Proceedings of the Combustion Institute 28:407.

Wolfrum (1998) "Lasers in Combustion: From Basic Theory to Practical Devices" 27th Symposium on Combustion pp. 1-41.

Docquier and Candel (2002) "Combustion control and sensors: a review" Progress in Energy and Combustion Science 28, 107-150.

English translation of a Japanese Office action received Apr. 8, 2010 for corresponding JP Application No. 2007-506152.

English translation of Chinese Office action received Mar. 25, 2010 for corresponding CN Application No. 200580010448.0.

* cited by examiner

OPTICAL MODE NOISE AVERAGING DEVICE

RELATED APPLICATIONS

This application is a 371 of International Application Number PCT/US2005/002853 filed Feb. 2, 2005, entitled "Optical Mode Noise Averaging Device," which claims priority to International Application Number PCT/US04/10048 filed Mar. 31, 2004 entitled "Method And Apparatus For The Monitoring And Control Of Combustion" which claims priority to U.S. Provisional Application No. 60/459,108 filed on Mar. 31, 2003 entitled "Echelle Grating Optical Multiplexer with Widely Spaced Wavelengths" each of which is incorporated herein in their entirety by reference.

TECHNICAL FIELD

The present invention is directed toward combustion monitoring, and more particularly toward an apparatus and method for averaging mode noise associated with a multimode optical fiber.

BACKGROUND ART

A large percentage of the electrical power generated in the United States of America is created in coal combustion power plants. The bulk of worldwide electricity production similarly relies on coal as a primary energy source. It is likely that coal will remain a primary energy source in the foreseeable future given the long term environmental concerns with the storage of waste from nuclear energy generation operations and the inefficiencies associated with solar powered electrical generation. In addition, vast worldwide coal reserves exist sufficient for at least 200 years of energy production at current rates.

However, there is and will continue to be a high demand to reduce the emissions of pollutants associated with coal-fired electrical energy generation and to increase the overall efficiency of the coal-fired generation process. Traditionally, in power plants and other industrial combustion settings, the efficiency of the combustion process and the level of pollution emission have been determined indirectly through measurements taken on extracted gas samples with techniques such as non-dispersive infrared (NDIR) photometry. Extractive sampling systems are not particularly well suited to closed loop control of a combustion process since a significant delay can be introduced between the time of gas extraction and the ultimate analysis. In addition, extractive processes generally result in a single point measurement which may or may not be representative of the actual concentration of the measured species within what can be a highly variable and dynamic combustion process chamber.

Laser-based optical molecular species sensors have recently been implemented to address the concerns associated with extraction measurement techniques. Laser-based measurement techniques can be implemented in situ and offer the further advantage of high-speed feedback suitable for dynamic process control. A particularly promising technique for measuring combustion gas composition, temperature and other combustion parameters is tunable diode laser absorption spectroscopy (TDLAS). TDLAS is well suited for the control and monitoring of coal-fired combustion processes. TDLAS is equally well suited for the monitoring of other combustion processes. In particular, the spectroscopy techniques described herein are useful for monitoring and controlling jet aircraft engine combustion parameters. TDLAS is typically implemented with diode lasers operating in the near-infrared and mid-infrared spectral regions. Suitable lasers have been extensively developed for use in the telecommunications industry and are, therefore, readily available for TDLAS applications. Various techniques of TDLAS which are more or less suitable for the sensing and control of combustion processes have been developed. Commonly known techniques are wavelength modulation spectroscopy, frequency modulation spectroscopy and direct absorption spectroscopy. Each of these techniques is based upon a predetermined relationship between the quantity and nature of laser light received by a detector after the light has been transmitted through a combustion process chamber and absorbed in specific spectral bands which are characteristic of the gases present in the process or combustion chamber. The absorption spectrum received by the detector is used to determine the quantity of the gas species under analysis plus associated combustion parameters such as temperature.

Typical coal-fired power plants have combustion chamber dimensions of 10-20 meters on a side. The plants are fired by pulverized coal, which results in a combustion process which both obscures the transmission of laser light because of the high dust load and which is extremely luminous. The environment is also highly turbulent. The overall transmission rate of light through the process chamber will fluctuate dramatically over time as a result of broadband absorption, scattering by particles or beam steering owing to refractive-index fluctuations. There is also intense thermal background radiation from the burning coal particles which can interfere with detector signals. The environment outside of the power plant boiler also makes the implementation of a TDLAS sensing or control system problematic. For example, any electronics, optics or other sensitive spectroscopy components must be positioned away from intense heat, or adequately shielded and cooled. Even though the implementation of a TDLAS system is extremely difficult under these conditions, TDLAS is particularly well suited to monitor and control a coal combustion process.

As discussed in detail in International Patent Application Serial Number PCT/US04/10048 (Publication Number WO 2004/090496), entitled METHOD AND APPARATUS FOR THE MONITORING AND CONTROL OF COMBUSTION, filed Mar. 31, 2004, which application is incorporated herein by reference in its entirety, optical fiber coupling is particularly advantageous for the implementation of a TDLAS system. In a fiber-coupled system, one or more probe beams which may consist of multiplexed light of various relevant wavelengths are delivered to a pitch-side (transmit) optical apparatus and projected into the combustion chamber. The probe beam is received in a catch-side (receive) optical apparatus after transversing the combustion chamber. As detailed in International Patent Application Serial Number PCT/US04/10048, it is advantageous to use a multimode optical fiber in the catch-side optical train. The use of a multimode fiber necessarily results in mode noise, which is a change in the signal level of detected light that results from non-uniform time and wavelength varying light distribution in the core of the multimode fiber used to collect and transport light. "Catch"-side mode noise can obscure absorption features which must be observed for effective TDLAS.

The phenomenon of mode noise is not limited to or caused by TDLAS implementations which feature a catch-side multimode optical fiber. On the contrary, mode noise will inevitably occur in any multimode optical fiber of substantial length which is transmitting light. Mode noise is inevitable in a multimode fiber because the greater cross sectional diameter of a multimode fiber as compared to a single-mode fiber allows transmitted light to propagate along numerous light paths or modes. Some paths or modes are longer or shorter than others. Thus, constructive and destructive interference necessarily occur resulting in non-uniform time and wavelength varying light distribution in the core of the multimode fiber which gives rise to a typical mode noise speckle pattern. Thus, mode noise occurs in computing, telecommunication, or other scientific applications utilizing substantial lengths of multimode fiber. Whether or not mode noise interferes with the efficiency of a given optical system depends upon the requirements of the particular system.

The present invention is directed toward overcoming one or more of the problems discussed above.

SUMMARY OF THE INVENTION

The present invention is an optical mode noise averaging device including a multimode optical fiber and means for averaging a modal-noise-induced signal level variation of light propagating within the multimode optical fiber. The device may average modal noise induced signal level variations by cyclically varying an index of refraction of the multimode optical fiber over a select period of time, scrambling a light distribution within the multimode optical fiber, or both. The index of refraction of the multimode optical fiber may be cyclically varied by cyclically varying the temperature of the multimode optical fiber. The index of refraction may be varied or the light distribution within the multimode optical fiber may be scrambled by cyclically and physically manipulating the multimode optical fiber.

The temperature of the multimode optical fiber may be varied through the action of a thermal element placed in thermal communication with the multimode optical fiber. Suitable devices for use as a thermal element include, but are not limited to, a thermoelectric module, a resistive heater, an infrared heater, a chemical heater, a conventional refrigeration device, a chemical cooler, a source of fluid cooled below ambient temperature, or a source of fluid heated above ambient temperature.

The optical device may include a temperature sensor such as a thermocouple in thermal contact with the multimode optical fiber and a controller receiving input from the temperature sensor and controlling the thermal element.

In an alternative embodiment which features an apparatus for cyclically manipulating the multimode optical fiber, the manipulation may include twisting, stretching, or shaking the multimode optical fiber. A piezo stretcher may be used to accomplish the cyclical stretching of the multimode optical fiber. Alternatively, a motor may be used to cyclically twist a portion of the multimode optical fiber in alternate clockwise and counterclockwise directions with respect to the longitudinal axis of the fiber and relative to a fixed portion of the fiber.

The present invention is further directed to a method of optical mode noise averaging in a multimode optical fiber including coupling light to the input of a multimode optical fiber, cyclically varying an index of refraction of the multimode optical fiber, and receiving the averaged light at the output of the multimode optical fiber. The method of mode noise averaging may include varying the index of refraction by one of cyclically varying the temperature of the multimode optical fiber and cyclically manipulating the multimode optical fiber. The temperature of the multimode optical fiber may be cyclically varied by providing a thermal component in thermal communication with the multimode optical fiber. Alternatively, the multimode optical fiber may be cyclically manipulated by twisting, stretching, or shaking the multimode optical fiber.

DETAILED DESCRIPTION OF THE PREFERRED EMBODIMENT

A. Overview

A preferred embodiment of the present invention is an optical mode noise averaging apparatus. The optical mode noise averaging apparatus is described in detail in Section E below. The optical mode noise averaging apparatus is particularly well suited to, but not limited to, averaging the mode noise which is inherent in a catch-side (or receive side) multimode optical fiber associated with a fiber-coupled tunable diode laser absorption spectroscopy (TDLAS) sensing apparatus. Multiple embodiments of such a sensing apparatus are discussed in detail in International Patent Application Serial Number PCT/US04/10048 (Publication Number WO 2004/090496), entitled METHOD AND APPARATUS FOR THE MONITORING AND CONTROL OF COMBUSTION, filed Mar. 31, 2004, which application is incorporated herein by reference in its entirety. In addition, a fiber-coupled TDLAS sensing apparatus is described below. The preferred embodiments of the present invention are suitable for averaging optical mode noise in any optical system where mode noise is present. In particular, the optical mode noise averaging apparatus may be implemented in any computing, telecommunications, scientific research, or other system which features a significant length of multimode optical fiber transmitting light. The averaging apparatus will be useful in any optical system where the efficiency of the system can be enhanced by averaging the optical mode noise inherent in light propagating within a multimode optical fiber.

B. Sensing Apparatus

Figure 1:
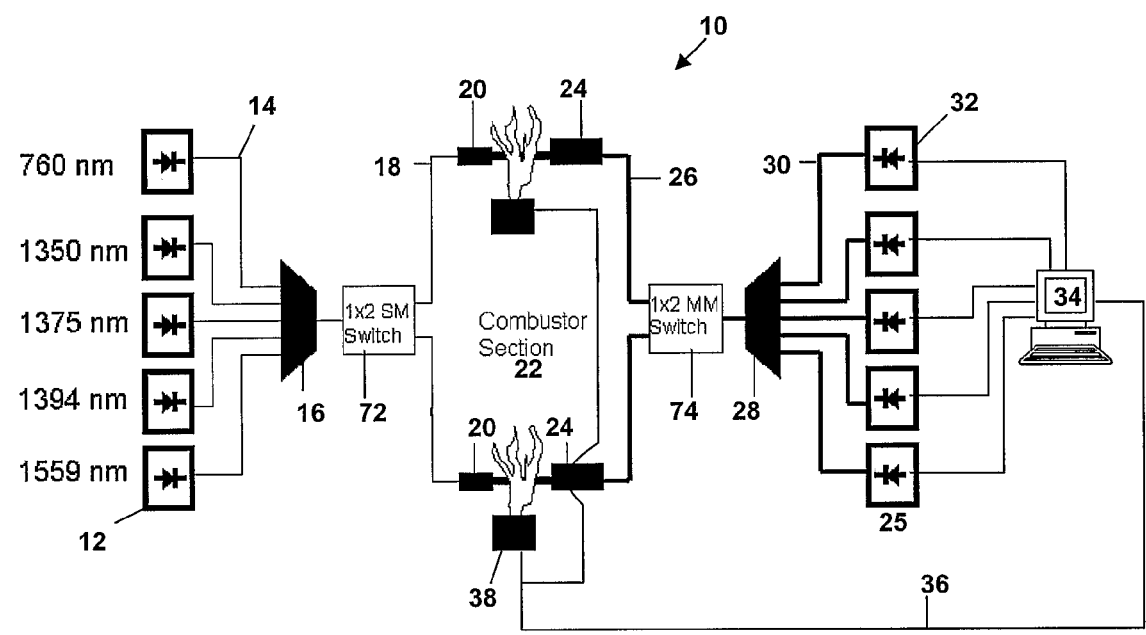
FIG. 1 is a schematic diagram of a TDLAS sensing apparatus.

An embodiment of a sensing apparatus 10 suitable for the sensing, monitoring and control of a combustion process is shown in FIG. 1. The sensing apparatus 10 performs tunable diode laser absorption spectroscopy (TDLAS) using laser light from a series of tunable diode lasers 12 lasing at select frequencies in the near-infrared or mid-infrared spectrum. The output of each tunable diode laser 12 is coupled to an individual optical fiber which may be a single-mode optical fiber 14 and routed to a multiplexer 16. As used herein, "coupled", "optically coupled" or "in optical communication with" is defined as a functional relationship between counterparts where light can pass from a first component to a second component either through or not through intermediate components or free space. Within the multiplexer 16 the laser light of some or all of the frequencies generated is multiplexed to form a multiplexed probe beam having multiple select frequencies. The multiplexed probe beam is coupled to a pitch-side (or transmit side) optical fiber 18 and transmitted to a pitch optic 20 or collimator operatively associated with a process chamber which, in FIG. 1, is shown as a combustion chamber 22.

The pitch optic 20 is oriented to project the multiplexed probe beam through the combustion chamber 22. Across the combustion chamber 22 in optical communication with the pitch optic 20 is a catch optic 24. The catch optic 24' is preferably substantially opposite the pitch optic 20 and is operatively associated with the combustion chamber 22. The catch optic 24 is positioned and oriented to receive the multiplexed probe beam projected through the combustion chamber 22. The catch optic 24 is optically coupled to a catch-side optical fiber 26 which transmits the portion of the multiplexed probe beam which is received by the catch optic 24 to a demultiplexer 28. Within the demultiplexer 28 the portion of the multiplexed probe beam received by the catch optic 24 is demultiplexed and each wavelength of demultiplexed laser light is coupled to an output optical fiber 30. Each output optical fiber 30 in turn is optically coupled to a detector 32, which typically is a photodetector sensitive to one of the select frequencies of laser light generated and multiplexed to form the probe beam. The detectors 32 generate an electrical signal based upon the nature and quantity of light transmitted to the detector 32 at the detector frequency. The electrical signal from each detector 32 is typically digitized and analyzed in data processing system 34. As discussed in detail below, the digitized and analyzed data can be used to sense physical parameters within the process chamber including but not limited to the concentrations of various gas species and the combustion temperature within the combustion chamber 22. The data processing system 34 can further be used to send signals through a feedback loop 36 to combustion control apparatus 38 and thereby actively control select process parameters. In the case of a combustion process, the process parameters controlled can include fuel (e.g., pulverized coal) feed rates; oxygen feed rates and catalyst or chemical agent addition rates. The use of fiber-optic coupling of the electronic and optical components on both the pitch and catch-sides of the sensing apparatus 10 allows delicate and temperature sensitive apparatus such as the tunable diode lasers 12, detectors 32 and data processing system 34 to be located in a control room having a stable operating environment. Thus, only the relatively robust pitch and catch optics 20, 24 need be situated near the hostile environment of the combustion chamber 22.

Figure 2:
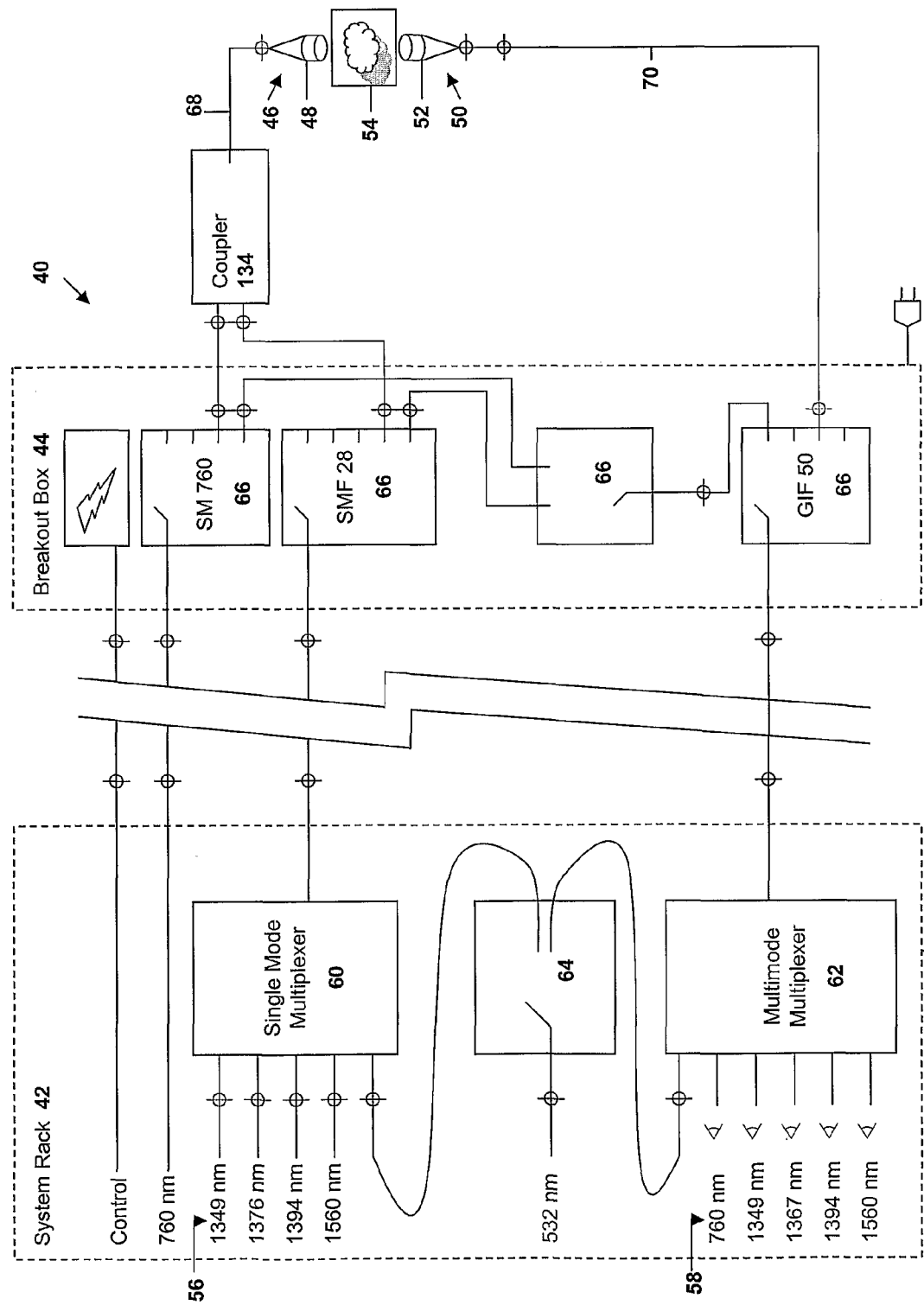
FIG. 2 is a schematic diagram of a TDLAS sensing apparatus featuring remotely located components optically coupled to components near a combustion chamber.

FIG. 2 schematically depicts the overall component placement of a fiber-coupled, multiplexed sensing system 40. The sensing system 40 generally consists of a system rack 42, a breakout box 44, a transmitter head 46 having pitch optics 48, a receiver head having catch optics 52 and connecting optical fibers. The system rack 42 is preferably located in a remote control room situated a distance, for example one kilometer, from the combustion chamber 54. The control room typically will have a moderate controlled environment. The system rack 42 contains the lasers 56, detectors 58, wavelength multiplexers 60 and wavelength demultiplexers 62. The system rack 42 also houses the system electronics and control software (not shown in FIG. 2). The system rack 42 may optionally house an alignment light source 64.

The optical fibers connecting the system rack 42 with the breakout box 44 are typically standard single-mode telecom optical fiber. This type of fiber is inexpensive, readily available, low-loss and allows the laser light to be directed to various off-the-shelf telecom components to manipulate the light, such as optical switches, splitters, and wavelength division multiplexers. Without optical fiber coupling, the laser light would have to be directed through free space all the way to the combustion chamber 54, which would be very difficult to implement or, alternatively, sensitive electronic and optical components would have to be situated in close proximity to the combustion chamber 54.

Also shown in FIG. 2 is a breakout box 44. The breakout box 44 is a ruggedized enclosure located close to the boiler. The breakout box 44 contains optical switches, splitters and couplers (collectively 66) which may be used as discussed below to direct the optical signals to multiple transmitter-receiver head pairs.

A third group of system components as shown in FIG. 2 are the transmitter and receiver heads 46, 50. The optics and electronics in the transmitter and receiver heads 46, 50 must convert the light in the fiber 68 into a collimated beam, direct the beam accurately through the combustion chamber 54, capture the beam on the far side of the combustion chamber 54 and couple the beam into the fiber 70. The choice of optics to accomplish this is determined by the transmission distance, the turbulence of the combustion zone, its effect on the transmitted beam's quality, and the core size of the fiber 70. Selection of the core size is a matter of design choice dictated by the application. A larger core will capture more of the laser light but also much more of the background light. When used with a coal-fired boiler, a fiber core diameter of 50 microns has provided acceptable results. Fiber coupling on the catch (receiver) side has several advantages. In particular, only light in the same location as the laser light and traveling in the same direction is focused into the fiber 70. This drastically reduces the amount of background light that is sensed. Light may be captured into one of several receiver fibers and an optical switch or other optical routing device can select light from one fiber for routing to the detectors 58. Only one catch optic is shown in FIG. 2.

The use of fiber coupling at the catch-side requires that the alignment tolerances of both the transmitter and receiver optics be precisely maintained (less than 0.5 milliradian for both the transmitter and receiver pointing). Preferably, both the pitch and catch optics 48, 52 are custom-designed and aberration-corrected for wavelengths from 660 nm to 1650 nm so that multiple laser signals can be efficiently transmitted and received at the same time.

C. Tunable Diode Laser Absorption Spectroscopy

Tunable diode laser absorption spectroscopy (TDLAS) is performed using techniques known to those skilled in the art of laser spectroscopy. Generally, TDLAS is performed by the transmission of laser light through a target environment, followed by the detection of the absorption of the laser light at specific wavelengths, due to target gases such as carbon monoxide or oxygen. Spectral analysis of the detected light allows identification of the type and quantity of gas along the laser path. The details of direct absorption spectroscopy are discussed in Teichert, Fernholz, and Ebert, "Simultaneous in situ Measurement of CO, H$_2$O, and Gas Temperature in a Full-Sized, Coal-Fired Power Plant by Near-Infrared Diode Lasers," (Applied Optics, 42(12):2043, 20 Apr. 2003), which reference is incorporated herein by reference in its entirety. The non-contact nature of laser absorption spectroscopy makes it well suited for harsh environments such as the combustion zone of a coal-fired power plant, or flammable or toxic environments where other probes cannot be used. The use of laser light provides the high brightness necessary to receive detectable transmission in the presence of severe attenuation (typically greater than 99.9% loss of light) that may be seen in some of these environments. To better withstand the harsh conditions of the target applications, the laser light may be brought in to the target environment through armored optical fiber.

Effective sensing of temperature or multiple combustion process component gasses requires the performance of TDLAS with multiple widely spaced frequencies of laser light. The frequencies selected must match the absorption lines of the transitions being monitored. For example, it is useful to monitor NO$_2$ at a wavelength of 670 nm to approximate emission NO concentrations. It is also quite useful to monitor oxygen, water vapor (temperature), and carbon monoxide in a coal-fired utility boiler. Suitable absorption lines, and thus suitable lasing frequencies can be selected based upon an assumption that the laser probe path length through a combustion chamber is equal to 10 meters and that the mole fraction of each species is CO (1%), O$_2$ (4%), CO$_2$ (10%), and H$_2$O (10%). For frequency selection purposes, the process temperature can be assumed to be 1800 K which is slightly higher than what is typically observed in a coal-fired plant, but the cushion serves as a safety factor in the calculations.

For example, three water absorption lines can be selected for TDLAS that meet the following criteria:
1. lower state energy of ~1000, 2000, and 3000 cm$^{-1}$, respectively;
2. provides a convenient absorbance of around 0.1-0.4 that, in turn, leads to approximately 20% beam absorption on resonance;
3. the optimum situation is to utilize transitions in the 1250 to 1650 nm region where inexpensive, high power, DFB diode telecommunications lasers are available;
4. the transitions must be well separated to allow for easy multiplexing; and
5. the selected wavelength must be efficiently diffracted by existing (de)multiplexer gratings.

Suitable water lines occur at the following wavelengths:

TABLE 1

| Wavelength (nm) | Wavenumber (cm$^{-1}$) | Lower State Energy (cm$^{-1}$) | Grating Order | Absorption at 1800 K and 10 M | UNP Grating Efficiency (model) |
|---|---|---|---|---|---|
| 1349.0849 | 7412.432 | 1806.67 | 6.87 | 19.7% | 81% |
| 1376.4507 | 7265.062 | 3381.662 | 6.73 | 28.1% | 77% |
| 1394.5305 | 7170.872 | 1045.058 | 6.65 | 6.8% | 72% |

No interference from any other combustion gases is anticipated. The most likely species to interfere, CO$_2$, was modeled and there are no strong, interfering lines in the 1.3-1.4 micron region.

Similarly, a suitable carbon monoxide line can be selected based on the work of Ebert referenced and incorporated above. A suitable carbon monoxide line is found at 1559.562 nm using the R(24) line in a coal-fired utility boiler. Selection of this line avoids interference from water and carbon dioxide. Known gratings are quite efficient in this wavelength region since it is in the optical communications C band. The absorbance of CO at this wavelength is expected to be 0.7%.

In addition, oxygen can be measured at 760.0932 nm. The preferred (de)multiplexing grating efficiency calculates to be only 40% in this region, however, suitable laser power should be available for reasonable measurement efficiency.

As discussed herein, the use of fiber coupling on both the pitch and catch-sides of a TDLAS sensing apparatus requires critical alignment of the pitch and catch optics. Active alignment is preferably accomplished with a select alignment wavelength. One possible alignment wavelength is 660 nm because high power (45 mW) diodes are available at this frequency and 660 nm would be near the peak of 14th order grating operation. Other alignment wavelengths may be determined to be equally or more suitable.

In summary, a reasonable set of wavelengths selected for multiplexing to a probe beam for TDLAS as embodied in the present invention are as shown in Table 2. It should be noted that this wavelength set is for one embodiment of a TDLAS sensing apparatus suitable for the sensing and control of a coal-fired power plant. Other wavelength sets can be equally suitable.

TABLE 2

| Purpose | Wavelength (nm) |
|---|---|
| Alignment | 660 |
| O$_2$ b-a band | 760.0932 |
| H$_2$O (moderate temperature line) | 1349.0849 |
| H$_2$O (high temperature line) | 1376.4507 |
| H$_2$O (low temperature line) | 1394.5305 |
| CO R(24) of (2, 0) overtone | 1559.562 |

D. Specific Benefits of TDLAS Using Multiplexed Beam

A particular advantage of TDLAS with a wavelength-multiplexed probe beam is increased accuracy of temperature measurements. In order to make accurate concentration measurements with TDLAS, the temperature of the monitored gas must be known. The strength of a molecular absorption is a function of temperature. Thus, to convert the amplitude of an absorption feature to concentration, the temperature must be known. Certain previous attempts to measure the concentration of combustion species such as CO suffer from insufficiently accurate temperature measurements leading to errors in quantification. This is particularly true for diode-laser-based ammonia slip monitors that have traditionally not incorporated temperature measurement at all. In the sensing system of the present invention, temperature may be determined by measuring the ratio of the intensity of two or more molecular water lines. The ratio of the integrated intensity of two lines is a function of temperature only (assuming constant total system pressure). Thus, in principle, two lines provide an accurate temperature. However, in the case of a non-uniform temperature distribution (as is typically found within an industrial combustion process), two lines do not suffice to determine the temperature distribution. In such a non-uniform temperature distribution, two lines can only determine a "path-averaged" temperature. In contrast, measuring the integrated amplitude of more than two lines (of the same species) allows temperature non-uniformity to be probed. An example of this technique has been demonstrated using oxygen as the probe molecule by Sanders, Wang, Jeffries and Hanson (Applied Optics, 40(24):4404, 20 Aug. 2001), which reference is incorporated herein by reference in its entirety. The preferred technique relies on the fact that the distribution of peak intensities measured along a line of sight is not the same for a path at an average temperature of 500 K, for example, as it is where one half of the path is at 300 K and the other half is at 700 K.

In addition to the benefit of more accurate temperature measurement, the use of a multiplexed probe beam can allow for the simultaneous monitoring of more than one combustion gas species, allowing for more refined control over the combustion process.

E. Mode Noise

The optical train of a TDLAS system and similar implementations which require a signal multiplexed from widely spaced wavelengths presents many design challenges due to the opposing design requirements of the reduction of mode noise and high efficiency light collection. Mode noise is defined herein as a change in the signal level of detected light that results from non-uniform time and wavelength varying light distribution in the core of a fiber used to collect and transport the light to and from the process chamber being measured.

In a multimode fiber, different modes propagate at different velocities due to refractive index variations. The intensity distribution in the fiber is then a speckle pattern resulting from interference of all the propagating modes that have undergone different effective path lengths. If all light in the speckle pattern is collected and detected, then constructive and destructive interference cancel exactly and the total transmitted power does not depend on wavelength or fiber length. If clipping, vignetting or other loss is introduced, the exact cancellation fails and the detected power changes with wavelength and/or time. In a TDLAS sensing system such as is described above, the power changes resulting from mode noise are quite problematic. Certain spectroscopy techniques rely on absorption of specific wavelengths of light by the gas species being studied. The absorptions are detected by a decrease in power at the critical wavelength. Thus, mode noise can mimic the power drop associated with absorption and obscure the data collected through TDLAS. A general expression for the detected power after a length, z, of fiber is:

$$P = P_0 + \Sigma_{ij} c_{ij} E_i E_j \cos[(2\pi v_0 \Delta n_{ij} z/c + \Delta \Phi_{ij}(T,\sigma))] \quad (1)$$

where
- $P_0$ = wavelength independent average power
- $E_i$ = amplitude of light n the ith transverse mode
- $c_{ij}$ = overlap integral between the ith and jth transverse mode
- $\Delta n_{ij}$ = refractive index difference between the ith and jth modes
- $\Delta \Phi_{ij}$ = phase shift between ith and jth modes due to temperature and stress For an orthonormal set of modes and no loss, $c_{ij}$=0. However, with any beam clipping or vignetting or any other mode dependent loss will cause some $c_{ij} \neq 0$. This will lead to ripples in the average transmitted power.

For a typical graded-index fiber with a 50 micron core, the total index change, $\Delta n$, is ~1%, but most modes spend the bulk of transmission time close to the fiber core center, and therefore, $\Delta n_{ij}$<0.0005, in general. The commonly available optical fiber GIF50 supports approximately 135 modes, which is sufficiently coarse to produce prominent mode noise during a wavelength scan given reasonably achievable beam clipping levels.

As a concrete modal noise example, one may consider the simplest possible system that exhibits mode noise: a rectangular waveguide supporting only the lowest mode in one dimension and only the two lowest modes in the orthogonal dimension:

Lowest mode: $E_1 = E_1^0 [\exp i(kz - \omega t)] \cos \pi x/2a$

Next mode: $E_2 = E_2^0 [\exp i(kz - \omega t)] \sin \pi x/a$

The intensity at a point z along the fiber is:

$$I(x) = |E_1 + E_2|^2 \text{ and the total power is } P = \int |E_1 + E_2|^2 dx \quad (2)$$

where the integral must include the effects of clipping and vignetting.

In the absence of clipping, $P \sim E_1^2 + E_2^2$ and there is no wavelength dependence. Adding clipping amounts to changing the limits of the integral. It can be shown that clipping results in an additional term $\sim E_1 E_2 \cos \Delta \Phi$ where $\Delta \Phi = \Delta k L = 2\pi \Delta n L/\lambda$.

If single-mode fiber could be used in the catch-side optical train of a system as described above, mode noise would not be an issue. However, multimode fiber must typically be used in the catch-side optical train of a fiber-coupled TDLAS system for two reasons. First, after traversing the measurement volume (a combustion chamber with a measurement path in excess of 10 meters), the initially single-mode (Gaussian spatial distribution) beam is significantly degraded in quality. Thus, the coupling efficiency of this severely distorted beam into single-mode fiber would be very poor. This is an unacceptable situation since the beam is attenuated by 3-4 orders of magnitude when passing through the measurement volume primarily due to scattering and obscuration by soot and fly ash. The additional attenuation resulting from using single-mode fiber would preclude measurement. Second, refractive beam steering effects in the fireball cause the position and pointing of the beam to be unstable. Given these effects, it would be difficult to "hit" the core of a single-mode fiber with any regularity.

On the other hand, the core of a multimode fiber presents at least 25 times the target cross sectional area of a single-mode fiber. Thus, the effects of beam steering can be significantly reduced. In addition, since the coupling efficiency into multimode fiber is independent of the spatial mode of the light, the poor beam quality obtained after passing through the fireball is not an issue.

Other types of implementations in the computing, telecommunications, or general scientific arts may have other similar or wholly unrelated restrictions which require or make advantageous the use of a substantial length of multimode optical fiber. In other implementations, mode noise may also be problematic and present significant data collection or data transmission challenges.

Thus, mode dependent losses occurring in the multimode fiber train are a significant design challenge. The light distribution emanating from the core of a multimode fiber exhibits a random speckle pattern, i.e., a random pattern of light and dark areas caused by constructive and destructive interference between different modes of the fiber. If the speckle pattern was totally invariant as a function of time and wavelength, it would not present a problem. However, slow variations in the speckle pattern particularly as a function of wavelength can cause mode noise if the beam is clipped anywhere in the multimode catch-side optical train as described above. This clipping is impossible to avoid; it can only be reduced. Therefore, additional measures to reduce mode noise must be implemented to improve the detection sensitivity of the system.

There are several ways in which to mitigate mode noise. From equation (2) above, mode noise may be reduced by:
1. reducing mode dependent losses, i.e., reducing clipping thereby keeping the $c_{ij}$ small;
2. reducing z, thereby increasing the period of the model noise to be much greater than the absorption lines of interest;
3. reducing $\Delta n_{ij}$ by using low dispersion fiber;
4. scrambling or phase shifting the modes; but not all mode scrambling or phase shifting techniques are equally effective, as is described below.

Preferably, the catch optics of a fiber-coupled TDLAS sensing system are designed and implemented to incorporate all of the above in order to reduce modal noise. The optics are designed such that any beam clipping should occur at a low level given near perfect alignment of the system. Efforts should be made to keep the length of multimode fiber to a minimum; however, for some applications z must be long in order to have the control electronics in an environmentally controlled area. The value of $\Delta n_{ij}$ may be reduced by using premium low-dispersion multimode fiber. In addition, excellent results may be obtained by averaging the modes by cyclically varying the index of refraction or mechanical manipulation of a catch-side multimode fiber and extracting data from the averaged light signal collected.

The speckle pattern exhibited in a multimode fiber varies as a function of time and wavelength and also as a function of the mechanical position of the fiber. Both transmission time and wavelength are affected by the index of refraction of the fiber. Flexing the fiber and manipulating it in specific ways can cause the speckle pattern to change. If these mechanical manipulations or a cyclic variation of the index of refraction are performed continuously, over a period of time, the spatial distribution of light emanating from the fiber averages to a relatively uniform pattern.

With effective cyclical phase shifting or scrambling of the modal noise, a time averaged measurement will produce a uniform signal level. The index of refraction of a fiber may be changed by stretching or twisting the fiber or varying the temperature of the fiber. Varying the temperature of the fiber causes a change in the refractive index difference between the ith and jth transverse modes, $\Delta n_{ij}$. This change in the index of refraction of the fiber shifts the modal noise by the function $\cos(2\pi v_0 \Delta n_{ij} z)/c$ given in equation 2.

F. Optical Mode Noise Averaging

Figure 3:
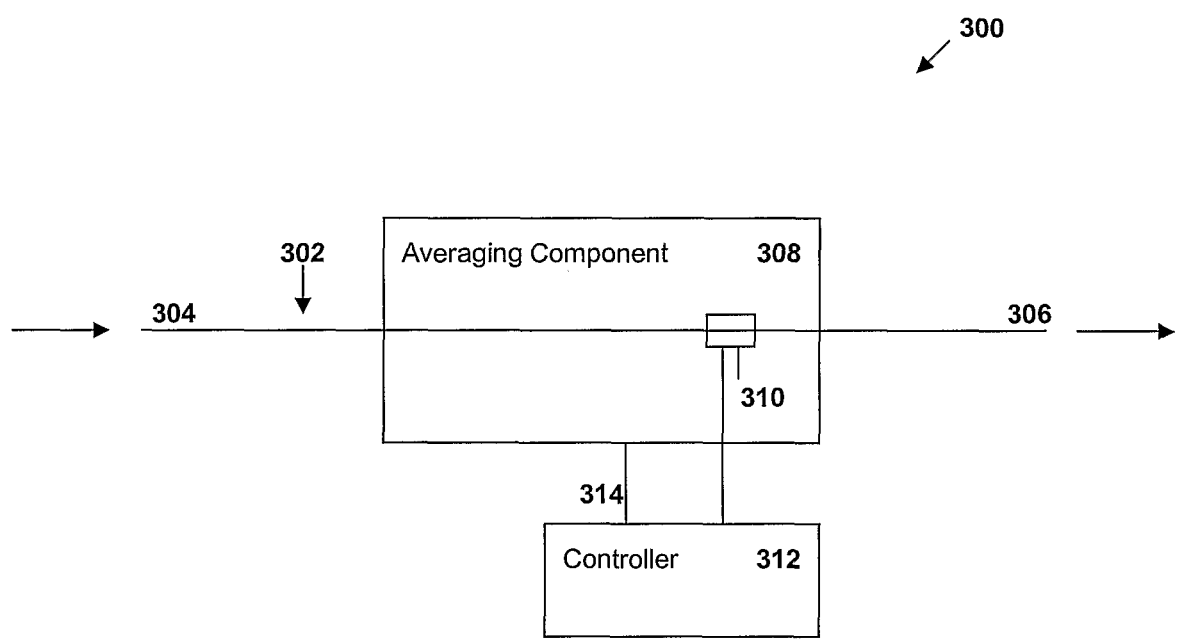
FIG. 3 is a schematic diagram of an optical mode noise averaging device consistent with the present invention.

As shown schematically in FIG. 3, the cyclical phase shifting or scrambling of modal noise to produce a time averaged measurement may be accomplished with an optical device 300. The optical device 300 will include a multimode optical fiber 302 having an input 304 and an output 306. Light may be coupled to the input 304 of the multimode optical fiber 302 and will generally propagate through the system in the direction of the arrows shown in FIG. 3 in association with the input 304 and the output 306.

The optical device 300 will also include an averaging component 308 operatively associated with the multimode fiber 302. The averaging component 308 may include apparatus for cyclically varying an index of refraction of the multimode optical fiber 302 over a select period of time. Alternatively, the averaging component 308 may include an apparatus for scrambling a light distribution within the multimode optical fiber 302. Variation of an index of refraction or scrambling a light distribution may be accomplished by the averaging component 308 through cyclically varying the temperature of the multimode optical fiber 302, cyclically manipulating the multimode optical fiber 302, or both.

In an embodiment where the averaging component 308 performs a cyclical manipulation of the multimode optical fiber 302, the averaging component 308 may twist, stretch, or shake the multimode optical fiber 302. In an embodiment where the averaging component 308 cyclically varies the temperature of the multimode optical fiber 302, various thermal elements or thermal components may be provided in thermal communication with the multimode optical fiber. Any apparatus which will affect the temperature of the multimode optical fiber 302 can be included in the averaging component 308. Representative devices which can be used to affect the temperature of the multimode optical fiber 302 include a thermoelectric module, a resistive heater, an infrared heater, a chemical heater, a conventional refrigeration device utilizing compressed fluids and heat exchangers, a chemical cooler, a source of fluid cooled below ambient temperature, and a source of fluid heated above ambient temperature. Some of these devices are discussed in detail below.

In an embodiment where the averaging component 308 causes cyclic heating or cooling of the multimode fiber 302, a sensor 310 may also be placed in thermal communication with the multimode optical fiber 302. The sensor 310 may provide information to a controller 312 which in turn may control the averaging component 308 through a control line 314.

G. Temperature-Based Phase Shifting Apparatus

The effectiveness of temperature-based modal phase shifting is directly related to the change in temperature per unit time and the length of the fiber, z, exposed to the temperature change. Temperature-based mode shifting is a particularly efficient method of dealing with modal noise because varying the temperature of the fiber changes in the index of refraction of all traverse modes and temperature changes can occur over a significant length of the fiber. Thus, by changing the index of refraction of the fiber, one guarantees that all transverse modes will shift, and no modes can remain 'frozen' with the signal.

Virtually any type of heating/cooling system can be placed in thermal communication with a multimode fiber to cycle the temperature of the fiber. Electric resistive heaters, conventional refrigeration devices, heated or cooled fluids, Peltier or other thermoelectric devices, infrared devices, or chemical devices could all be used to affect the temperature of a fiber.

Figure 4:
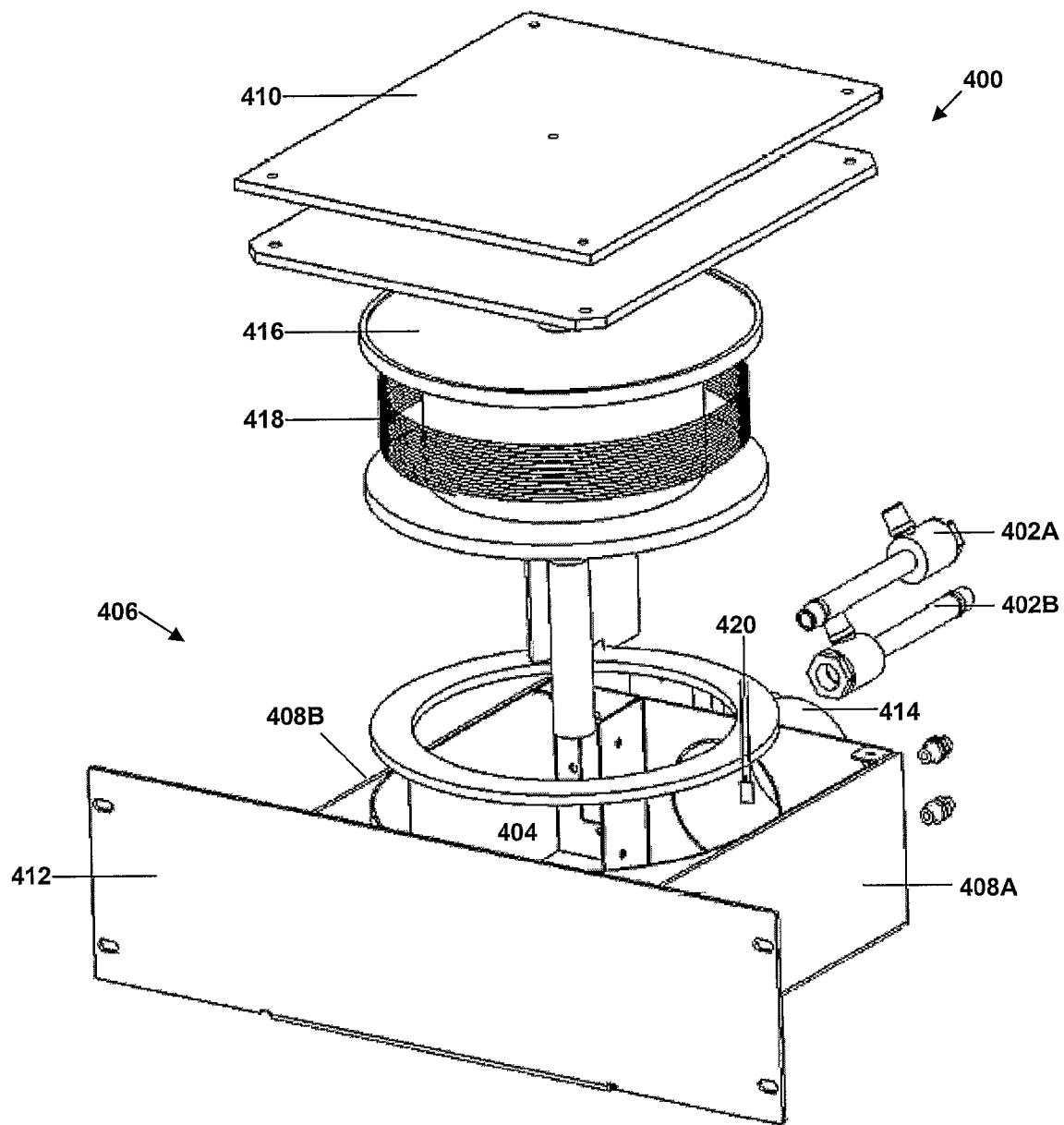
FIG. 4 is an exploded view of a temperature-based phase shifting apparatus with a source of fluid heated above or cooled below ambient temperature as a thermal element.

One embodiment of a modal phase shifting device which utilizes cyclic temperature changes is a fluid based modal phase shifting device (fluid device) 400. An exploded view is illustrated in FIG. 4. An embodiment of a fluid device 400 which uses vortex air tubes 402A, 402B to alternately blow hot and cold air across and around the fiber is shown in FIG.

4. Air delivered from a compressed air source (not shown in FIG. 4) is alternately delivered to one of two vortex tubes 402A, 402B. The vortex tubes 402A, 402B are coupled in fluid communication with the interior of a chamber 404. As shown in FIG. 4, the chamber 404 may be formed of an enclosure 406 having sides 408A, 408B, a top plate 410, a front 412, and a rear access port 414. The entire enclosure 406 may be suitable for rack mounting in a typical data processing equipment rack. Although a rack mountable enclosure 406 is particularly convenient, any enclosure shape, type, or style which is suitable for receiving a spool 416 holding a length of multimode optical fiber 418 may be used to implement the fluid device 400. Alternatively, a device without an enclosure 406 could be used.

The vortex tubes 402A, 402B are in fluid communication with the interior of the enclosure through access port 414, and are thus in fluid and thermal communication with the multimode optical fiber 418 wound onto the spool 416. Accordingly, the multimode optical fiber 418 may be cyclically heated and/or cooled by the application of air heated or cooled above or below ambient temperature by the vortex tubes 402A, 402B.

Suitable vortex tubes 402A, 402B are readily available. For example, EXAIR®3230 vortex tubes are available from EXAIR® Corporation. These or similar vortex tubes operating at 30 ft³/minute throughput can provide air heated to +60° C. or cooled to −20° C. depending on the orientation of the tube. In addition, it is relatively easy to cycle between heated and cooled air when using vortex tubes. It is important to note, however, that any apparatus or method of cyclically supplying a heated or cooled fluid in thermal communication with the multimode optical fiber 418 is suitable for the implementation of an embodiment of the fluid device 400. The heating and cooling fluid may be air as discussed above, however, water, heating/cooling oils, compressed gases, or other fluids may be used to heat or cool the multimode fiber.

By way of example, and not limited by, during operation, one of the vortex tubes 402A, 402B may deliver heated air until the fiber reaches a temperature about 10° C. greater than the inlet temperature. The temperature of the fiber may be determined by a thermocouple 420 or other temperature sensor embedded in contact with the fiber. A temperature control unit (not shown in FIG. 4) may receive input from the thermocouple 420 and trigger a solenoid switch so that air is sent to the other vortex tube 402A, 402B for cooling. Alternatively, because heated air provided to the multimode optical fiber 418 by the vortex tubes 402A, 402B will never reach critical levels, the use of temperature controller can be eliminated and replaced with a timed relay to cyclically switch the vortex tubes 402A, 402B between heating and cooling. Cycling between temperatures is preferably continuous during operation of the device.

Figure 5:
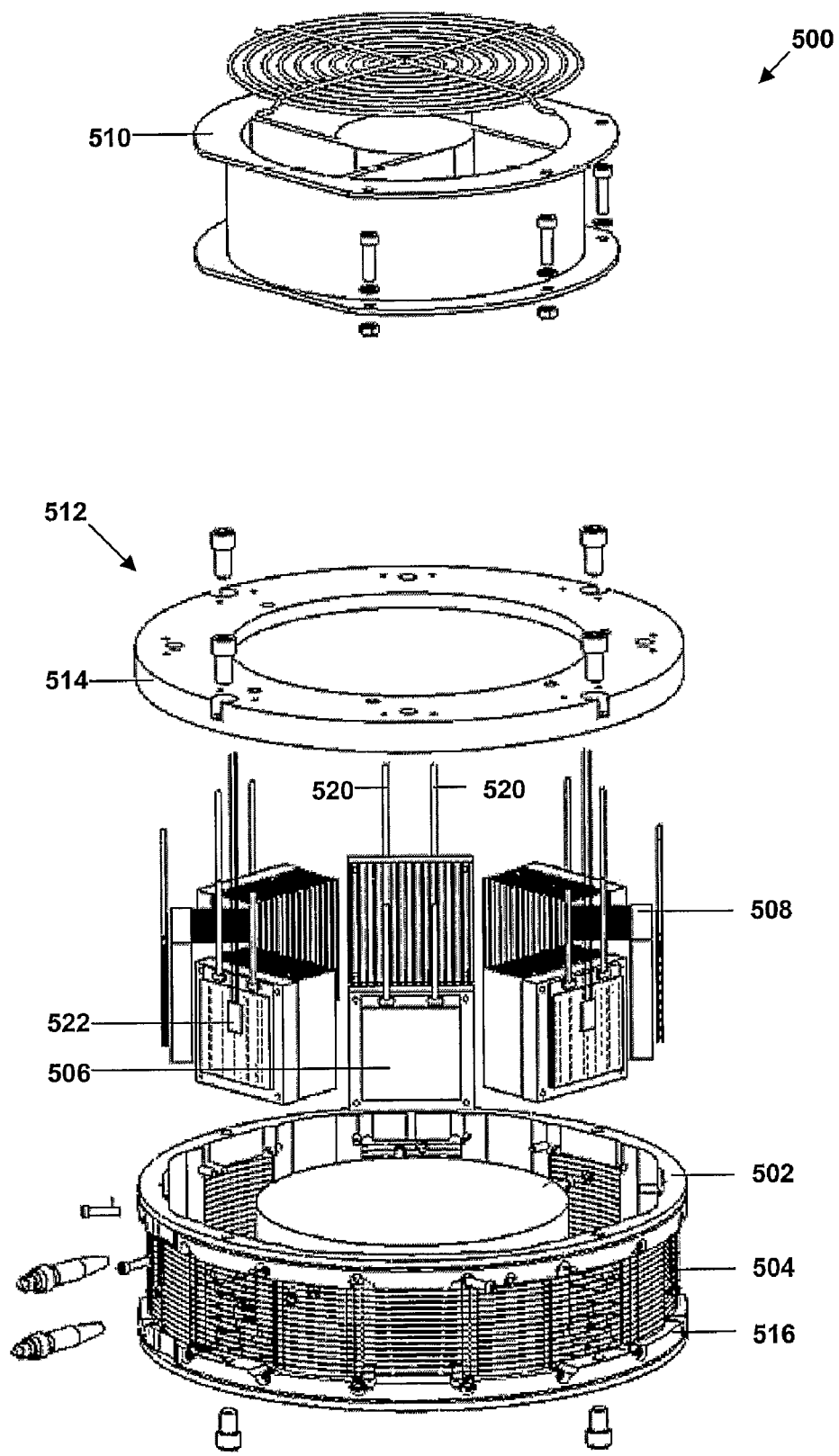
FIG. 5 is an exploded view of a temperature-based phase shifting apparatus utilizing a series of thermoelectric devices as the thermal element.
Figure 6:
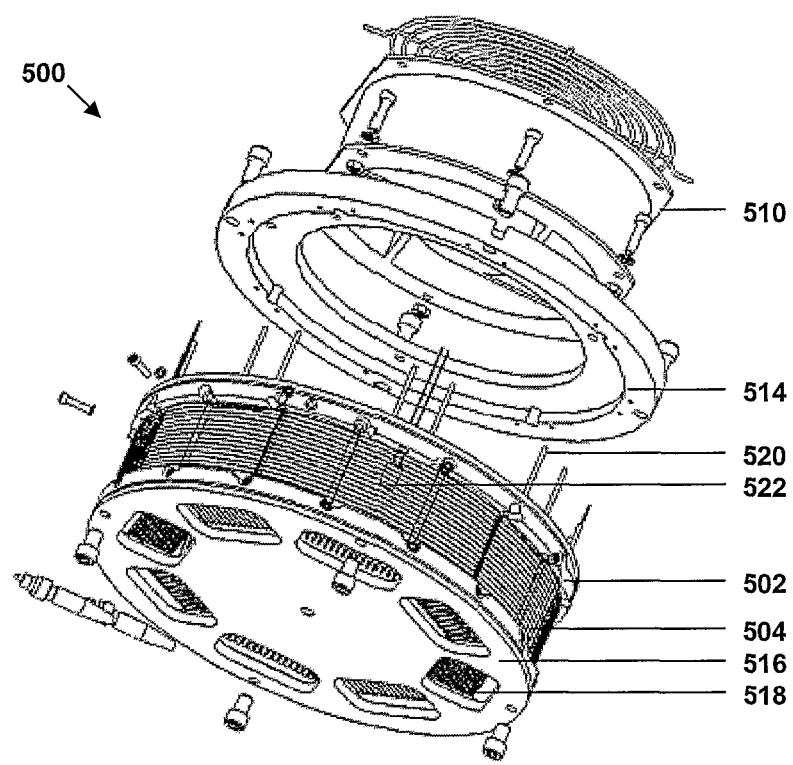
FIG. 6 is an alternative exploded view of the temperature-based phase shifting apparatus of FIG. 5.

A highly preferred embodiment of a modal phase shifting device which is based upon cyclically varying the temperature of a multimode fiber is shown in FIG. 5 and FIG. 6. The thermoelectric modal phase shifting device (thermoelectric device) 500 includes a spool 502 holding a select length of multimode optical fiber 504. One or more thermoelectric heating/cooling modules 506 are placed in thermal communication with the multimode optical fiber 504. In the embodiment shown in FIG. 5, multiple thermoelectric heating/cooling modules 506 are radially disposed around the inside of the spool 502. Thermal communication is facilitated by the use of thermoelectric grease between the outer surface of a thermoelectric module 506 and the coil of multimode optical fiber 504. In the embodiment shown in FIG. 5, the spool 502 is constructed with an open rim to facilitate contact between the thermoelectric modules 506 and the multimode optical fiber 504 and to facilitate winding the multimode optical fiber 504.

One arrangement for positioning of the thermoelectric modules 506 in contact with the multimode fiber 504 and relative to the spool 502 is illustrated in the exploded view of FIG. 6.

One or more heat sinks 508 may also be operatively disposed in thermal communication with the thermoelectric modules 506. Preferably, the heat sinks 508 are fabricated from a highly thermally conductive material such as aluminum or copper and have fins or other apparatus designed to increase the surface area of each heat sink 508. A fan 510 may be operatively positioned to force or draw air across the heat sinks 508, facilitating the rapid extraction of heat from the thermoelectric modules 506 and thus the rapid heating or cooling of the multimode fiber 504. As shown in FIG. 5 and FIG. 6, a framework 512 having a top ring 514 and a bottom ring 516 may be employed to hold the components of the thermoelectric device 500 in a proper orientation with respect to each other without hindering the flow of air over and around the heat sinks 508. Preferably, openings 518 are formed in the framework 512 to assure free airflow.

The embodiment illustrated in FIG. 5 and FIG. 6 uses thermoelectric modules 506 which are based upon the Peltier principle. Direct current is provided to a thermoelectric module 506 through leads 520. With a thermoelectric module 506 operating under the Peltier principle, opposite surfaces of the thermoelectric module 506 heat or cool depending on the direction of the DC current provided. Thus, these modules provide certain advantages because it is relatively easy to selectively heat or cool the multimode optical fiber 504 by selectively switching the polarity of the direct current provided to the leads 520. It is important to note, however, that other types of devices may be implemented to heat and/or cool the multimode optical fiber 504. For example, direct resistive heaters, conventional refrigeration apparatus, infrared heating devices, and/or chemical reaction based heaters and/or coolers could be used to vary the temperature of the multimode fiber 504.

In the preferred embodiment, power may be delivered from a suitable power supply to the thermoelectric modules 506 mounted in a cylindrical configuration as shown in FIG. 5 and FIG. 6. Current switching electronics may be used to cyclically reverse the polarity of the DC power delivered to each thermoelectric module 506. Modal phase shifting occurs in the length of multimode fiber 504, preferably Premium GIF50 multimode fiber, that is in thermal communication with the thermoelectric modules 506. 55 m to 100 m has been found to be a suitable length of multimode fiber to accomplish modal phase shifting and averaging. Other lengths may be suitable as well. If 100 m of wrapped fiber is used approximately 50% of the fiber is in direct contact with the thermoelectric coolers. By direct contact, it is noted that, besides thermoelectric grease, there is no conductive material between the thermoelectric modules 506 and the fibers 504. This configuration minimizes the thermal mass of the system. By minimizing the thermal mass the temperature response of the system is rapid and creates more efficient modal phase shifting.

One or more thermocouples 522 or other temperature measuring devices may be mounted between the thermoelectric modules 506 and the multimode optical fibers 504 and used to monitor the temperature of the multimode optical fiber 504 at all times. A temperature control unit (not shown in FIG. 5 and FIG. 6) may receive the thermocouple-determined temperature and cycle the current direction based on the temperature readings. Temperate ranges of about 35° C. to 50° C. are achievable with readily available thermoelectric modules. It is important that the fiber not exceed a maximum temperature of 85° C. or damage to the fiber could occur. Tests have been completed with temperature variation from 65° C. to 10° C. with single sided coolers and 65° C. to 30° C. with dual sided coolers. A complete cycle may be of any select duration, however, a cycle of approximately 25 seconds has been found to be effective.

As described above, heat may be dissipated on the opposite side of the thermoelectric modules 506 by means of heat sinks 508 mounted in thermal communication with the thermoelectric modules 506. Forced air may be fed or drawn through the heat sink fins to aid in the dissipation of heat equivalent to the input power. Efficient heat dissipation may be accomplished by forcing air through openings 518 at the bottom of the fins so that air flows through the system and out the top of the unit. Other configurations which allow sufficient airflow are suitable as well. Alternatively, the thermoelectric device 500 could be bathed in cooling fluid or otherwise cooled. Preferably, the fan is in constant operation while the device is running. Any suitable fan or fluid source may be utilized to dissipate heat, however, a 300CFM fan has been found effective to remove heat from the system as shown in FIG. 5 and FIG. 6.

Controlling electronics may be associated with heating and cooling of the thermoelectric modules 506. Feedback controlling electronics may sense the temperature of the fiber based upon input from the thermocouple 518, a thermometer, or other temperature sensor. In addition, based upon the temperature input, the controller may switch the current direction of power delivered to a thermoelectric module 506 and adjust power levels for the heating and cooling cycles (heating is typically more efficient so less power may be needed). Also, the controller may control the maximum and minimum temperatures delivered to the fiber-optics, and shut off the drive circuitry in the event of overheating.

H. Thermoelectric Module Phase Shift System Tests

Tests have been performed with the thermoelectric device 500 described above. Tests were performed by pitching four wavelength bands through an absorption free, nitrogen purged chamber. Without an absorption species in the pathlength, the laser should exhibit a linear wavelength response after being divided by a reference signal. The deviation in linearity of the slope is caused predominantly by modal noise. A general expression of the equation used to determine uncertainty in the measurement is given as:

$$\sigma_x = [1/N \Sigma (x_i - f_i(ax+b))^2]^{1/2} \quad (3)$$

where $x_i = signal_i/tap_i$ $f_i(ax+b) = $ linear fit of $x_{1-n}$

The start and end of each wavelength cycle may be neglected due to time delays cased by travel times of the pitch and receive heads. These time delays cause significant variation between the tap and observed signal at the start and end of each cycle.

System performance tests have been made with embodiments of the thermoelectric device 500 using single sided and double sided thermoelectric modules 506, multiple averaging times, and different fiber lengths. For all results, modal phase shifting and averaging produced reduced modal noise signal deviations. The reduction of noise was dependent on the length of fiber used in the experiment as given in equation (3); long fibers have more high frequency modal noise deviations than do short fibers. Because of this, the relative resolution enhancement of modal phase shifting is witnessed more in long fibers. Results are presented below for the various configurations:

TABLE 3

| Type | Average Time (seconds) | Uncertainty (ppm) | | | | Average Uncertainty |
|---|---|---|---|---|---|---|
| | | 1349 nm | 1376 nm | 1394 nm | 1560 nm | |
| 200 m of fiber unheated | — | 8792 | 19514 | 6838 | 13712 | 11715 |
| 30 m of fiber unheated | — | 3156 | 5174 | 5311 | 1231 | 4547 |
| 270 m of fiber unheated | 10 | 16837 | 24417 | 21989 | 14533 | 19444 |
| No modal scrambling, TEM turned off | | | | | | |
| | 3 | 1684 | 2394 | 3527 | 2647 | 2535 |
| | 10 | 612 | 966 | 3013 | 0 | 1530 |
| | 10 | 1229 | 1592 | 3084 | 0 | 1968 |
| | 10 | 1434 | 1581 | 1823 | 0 | 1613 |
| Single sided TEM, 100 m operative fiber length, 270 m total fiber length | | | | | | 1912 |
| 10° C.-65° C. temperature range | | | | | | Average |
| | 10 | 3048 | 3896 | 2020 | 1871 | 2709 |
| | 10 | 4213 | 2680 | 1856 | 3216 | 2991 |
| | 10 | 3317 | 1742 | 2257 | 2838 | 2538 |
| at turnaround | 1 | 4957 | 1628 | 1736 | 2939 | 2815 |
| Cool to hot | 1 | 2712 | 2490 | 1208 | 2345 | 2189 |
| Cool to hot | 1 | 3119 | 3559 | 4965 | 1921 | 3391 |
| Cool to hot | 1 | 2762 | 3163 | 3519 | 1541 | 2746 |
| Cool to hot | 1 | 2468 | 3388 | 1928 | 2887 | 2668 |
| Cool to hot | 1 | 3724 | 2479 | 2394 | 3005 | 2901 |
| Cool to hot | 1 | 2865 | 2363 | 2700 | 1917 | 2461 |
| Cool to hot | 1 | 5187 | 1924 | 2327 | 3633 | 3268 |
| Cool to hot | 1 | 3327 | 3392 | 1447 | 1777 | 2486 |
| Cool to hot | 1 | 4989 | 1556 | 2819 | 3090 | 3113 |
| Cool to hot | 1 | 2812 | 1985 | 1542 | 1642 | 1995 |
| 75 m of operative multimode fiber, 245 m total fiber length, single sided TEM, | | | | | | 2531 |
| 65° C.-10° C. temperature range | | | | | | Average |
| Cycled | 10 | 3975 | 3465 | 2375 | 3014 | 3207 |
| Cycled | 10 | 2997 | 963 | 1408 | 2085 | 1863 |

TABLE 3-continued

| Type | Average Time (seconds) | Uncertainty (ppm) | | | | Average Uncertainty |
| --- | --- | --- | --- | --- | --- | --- |
| | | 1349 nm | 1376 nm | 1394 nm | 1560 nm | |
| Cool to hot | 1 | 3111 | 1841 | 1538 | 2982 | 2368 |
| Cool to hot | 1 | 2268 | 1518 | 2365 | 2932 | 2271 |
| 55 m of operative multimode fiber, 225 m total fiber length, double sided TEM, 65° C.-30° C. temperature range | | | | | | 2167 Average |

Mechanical Manipulation Based Apparatus

As discussed above, mode noise may be averaged and smoothed by cyclically varying the index of refraction or by mechanical manipulation of a multimode fiber and extracting data from the average light signal collected. The temperature-based phase shifting apparatuses discussed above accomplish modal phase shifting by varying the index of refraction of a multimode fiber through cyclical temperature variations. As discussed below, mechanical manipulation of a multimode fiber may also be employed to vary the index of refraction. In addition, mechanical manipulation may result in averaging and smoothing of a mode-noise affected signal through light's inability to completely follow a particular mode within a waveguide as the fiber is manipulated. Thus, the averaging and smoothing of a mode noise induced speckle pattern within a length of multimode fiber may be accomplished by a combination of phase shifting and mechanical scrambling.

Some specific modes of mechanical fiber manipulation are more effective at averaging mode noise than others. In particular, twisting the fiber about its longitudinal (z) axis relative to some other point on the fiber causes the speckle pattern to change. The dominant change obtained is a rotation of the speckle pattern around the z-axis. Of interest is the fact that the pattern does not rotate as far around the axis as the fiber is mechanically rotated. A secondary effect is that the actual light distribution is somewhat altered by the rotation. The rotation of the speckle pattern is not predominantly due to stress induced refractive index changes in the fiber, although this may explain small changes in the speckle intensity pattern. Rather, the rotation is due to the light's inability to completely follow the waveguide as it is manipulated in a torsional motion.

Figure 7:
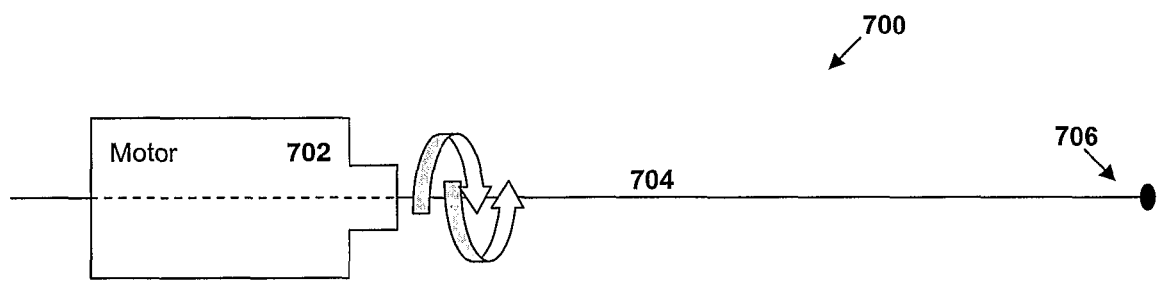
FIG. 7 is a schematic diagram of an optical mode noise averaging device using a motor for mechanical manipulation of a multimode optical fiber.

One embodiment of the present invention, a mechanical mode noise averaging apparatus (mechanical device) 700 is shown schematically in FIG. 7. The mechanical device 700 uses a hollow shaft motor 702 through which a multimode fiber 704 is placed and fastened. A remote section of fiber 706 is held fast relative to the shaft position of the motor 702, and the motor is repetitively swept through a twisting motion which is preferably +360 degrees and then −360 degrees of motion. The frequency of this motion preferably is greater than or equal to 10 Hz to enable effective averaging of the transmitted signal, and significantly reduce the effect of catch-side mode noise. Although the twisting of a multimode fiber along its longitudinal axis has been determined to be effective at scrambling mode noise, other mechanical manipulations such as shaking, stretching, or bending may be employed as well.

Piezo Stretcher

Stretching an optical fiber introduces both a change in the index of refraction and the length of the fiber. Multimode fiber can be stretched with a piezo stretcher. Piezo devices are generally used to introduce a modulated time delay in a single-mode fiber. Multimode fiber is not used in piezo stretching devices because time delays in multimode fiber are not controllable because of the multiple paths or modes that the light can travel. However, the piezo stretching devices, although not practical for producing a time delay, may be used to introduce modal phase shifts.

Figure 8:
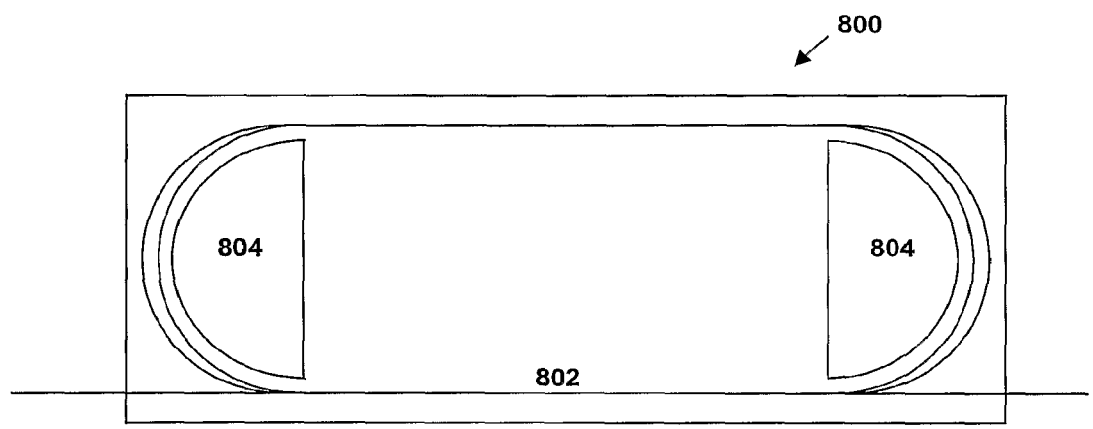
FIG. 8 is a schematic diagram of an optical mode noise averaging device using a piezo stretcher for mechanical manipulation of a multimode optical fiber.

When multimode fiber is stretched, stresses introduced on the fiber will cause a change in both the index of refraction and length of the fiber. As shown schematically in FIG. 8, a piezo device 800 works by winding several meters of multimode optical fiber 802 around half cylinders 804, and then oscillating the half cylinders 804 at a prescribed oscillation frequency and distance. As the distance between the half cylinders 804 expands and contracts, stresses in the fiber 802 harmonically oscillate. This oscillation causes the index of refraction of fiber 802 to fluctuate. The effectiveness of the modal shift is function of both the change in the length of the fiber (z) and the change in the index of refraction ($\Delta n_{ij}$) in the fiber (equation (1)).

Modal phase shifting can be accomplished by one of two techniques using a piezo device 800. For the first technique, a piezo device 800 is implemented with enough fiber 802 and configured to introduce enough stress to produce a great degree of modal variation so that a uniform signal level could be achieved by averaging the many modes. Alternatively, because the piezo device 800 cycles through steady index changes, a piezo device 800 could potentially be operated to oscillate in a manner that produces a mode shift of a harmonic of 180° at minimum and maximum stretching distances. By this method modal noise could be reduced, not by time averaging many mode shifts, but by optimizing the stretching characteristics so that a phase shift of 180° is achieved. Thus, modal noise could then be averaged in as little as one cycle, allowing for rapid data acquisition with modal noise elimination.

Pitch-Side Optical Train

The pitch-side optical train of a fiber-coupled TDLAS sensing apparatus also presents a significant design challenge due to the necessity of producing a single-mode beam for all wavelengths to be transmitted through the measurement region. If single-mode fiber could be used throughout the pitch-side optical train, mode noise would not be an issue. However, fiber only operates as a single-mode waveguide over a limited wavelength window. Beyond the short wavelength cutoff for a particular fiber, light can be transported through the fiber in several higher order spatial modes. These higher order modes will interfere to produce a speckle pattern when the light exits the fiber. The speckle pattern is time and wavelength varying. Even a small amount of beam clipping then gives rise to noise in the measurement.

On the contrary, if a fiber is selected that has a single-mode cutoff that matches the shortest wavelength that needs to be transmitted, the longer wavelengths will suffer a substantial loss when coupled into the fiber and the fiber will exhibit extensive bending losses for the longer wavelengths.

This problem can be acute in the fiber-coupled, wavelength multiplexed TDLAS sensing and control device described above due to the need to multiplex wavelengths as long as 1.67 microns with wavelengths as short as 760 nm or 670 nm. There is no known single commercially available fiber that will provide single-mode operation, high coupling efficiency and low bending losses for such a broad range of wavelengths. Photonic crystal fiber may in the future provide a solution to this dilemma, but photonic crystal fiber technology is currently in its infancy.

Figure 9:
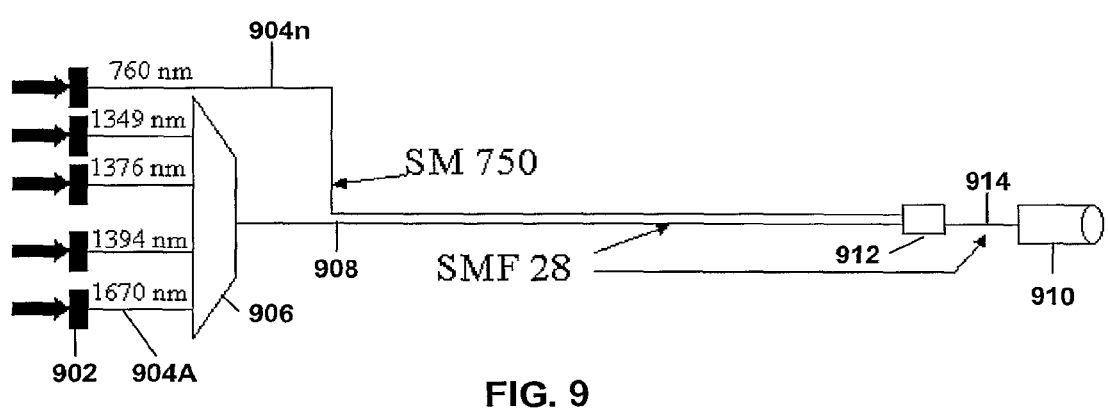
FIG. 9 is a schematic diagram of a pitch-side mode noise reduction device.

As shown in FIG. 9, the problem of multiplexing and pitching light in a single-mode beam from 670 nm or 760 nm to 1670 nm may be minimized by utilizing a very short transmission section of multimode fiber 120 that does not allow the higher order spatial modes for a wavelength shorter than the single-mode cutoff to develop. Referring to equation (1) above, if the length, L, of multimode fiber is short, then mode noise will be minimized. In this case, for example, if 760 nm light is coupled to a short section of single-mode fiber with a cutoff wavelength of 1280 nm (e.g., Corning SMF 28), the 760 mm light remains single-mode for at least a few meters. Therefore, a solution to pitch-side mode noise is to couple the 760 nm light into a fiber which is single-mode for wavelengths longer than 1280 nm but could be multimode for 760 nm, with only a short distance to traverse before it is collimated to be transmitted through the measurement zone.

A schematic diagram of such a system is shown in FIG. 9 and FIG. 2. Referring to FIG. 9, multiple diode laser sources 902 lasing at widely spaced lasing frequencies are coupled to discrete single-mode optical fibers 904A-904n. The diode lasers lasing at wavelengths between 1349 nm and 1670 nm are multiplexed with a multiplexer 906. The output of multiplexer 906 is coupled to a pitch-side fiber-optic 908 having suitable dimensions for transmitting light with wavelengths ranging from 1349 nm-1670 nm, both without substantial transmission losses and without the introduction of mode noise. A suitable fiber-optic for these wavelengths is Corning SMF28. However, the 760 nm input, if multiplexed and coupled to an SMF28 optical fiber would, after transmission over a relatively short distance, become multimodal. Accordingly, the output of the 760 nm laser is coupled to a fiber which is single-mode for wavelengths less than 1280 nm such as SMF750. The laser light transmitted in the input fiber 904n and the multiplexed laser light transmitted in the pitch-side optical fiber 908 can be coupled nearby the pitch optic 910. The coupler 912 and pitch optic 910 are preferably optically connected by a short length of transmission optical fiber 914 with the transmission optical fiber 914 being selected to transmit all of the coupled and multiplexed wavelengths without significant loss. A suitable transmission optical fiber for the system depicted in FIG. 9 would be Corning SMF28. Provided that the transmission optical fiber is relatively short, the 760 nm laser light coupled to the transmission optical fiber 914 will not exhibit significant multimodal behavior. For the system and fibers depicted in FIG. 9, it has been determined that the transmission optical fiber must be kept to a length of 3 meters or less to avoid the introduction of significant multimodal noise.

A similar system is shown in FIG. 2 where coupler 134 receives input from both a 760 nm diode laser and a multiplexed beam from diode lasers having substantially longer wavelengths.

The objects of the invention have been fully realized through the embodiments disclosed herein. Those skilled in the art will appreciate that the various aspects of the invention may be achieved through different embodiments without departing from the essential function of the invention. The particular embodiments are illustrative and not meant to limit the scope of the invention as set forth in the following claims.

What is claimed is:

1. An optical device comprising:
   a multimode optical fiber: and
   means for averaging a modal noise induced signal level variation of light propagating within the multimode optical fiber wherein the means for averaging comprises one of:
   means for cyclically varying an index of refraction of the multimode optical fiber over a select period of time; and
   means for scrambling a light distribution within the multimode optical fiber.

2. The optical device of claim 1 wherein the means for averaging comprises one of:
   means for cyclically varying the temperature of the multimode optical fiber; and
   means for cyclically manipulating the multimode optical fiber.

3. The optical device of claim 2 wherein the means for cyclically manipulating the multimode optical fiber comprises an apparatus configured to perform at least one of:
   twisting the multimode optical fiber;
   stretching the multimode optical fiber;
   shaking the multimode optical fiber.

4. The optical device of claim 2 wherein the means for cyclically varying the temperature of the multimode optical fiber comprises a thermal element in thermal communication with the multimode optical fiber, the thermal element comprising at least one of a heater, a cooler, a source of fluid heated above ambient temperature and a source of fluid cooled below ambient temperature.

5. The optical device of claim 2 further comprising:
   a temperature sensor in thermal contact with the multimode optical fiber; and
   a controller receiving input from the temperature sensor and controlling the means for cyclically varying the temperature of the multimode optical fiber.

6. A method of time averaging modal noise induced signal strength variations in multimode optical fiber having an input and an output, the method comprising:
   coupling light to the input of the multimode optical fiber;
   cyclically varying an index of refraction of the multimode optical fiber; and
   receiving the light at the output of the multimode optical fiber.

7. The method of claim 6 wherein the index of refraction of the multimode optical fiber is varied by one of:
   cyclically varying the temperature of the multimode optical fiber; and
   cyclically manipulating the multimode optical fiber.

8. The method of claim 7 wherein the step of cyclically varying the temperature of the multimode optical fiber comprises providing a thermal component in thermal communication with the multimode optical fiber.

9. The method of claim 8 further comprising:
   providing a temperature sensor in thermal communication with the multimode optical fiber; and
   controlling the thermal component with a controller receiving input from the temperature sensor.

10. The method of claim 7 wherein the step of cyclically manipulating the multimode optical fiber comprises at least one of:
    twisting the multimode optical fiber;
    stretching the multimode optical fiber;
    shaking the multimode optical fiber.

11. A combustion sensing apparatus comprising a catch-side optical system comprising:
a multimode optical fiber: and
means for averaging a modal noise induced signal level variation of light propagating within the multimode optical fiber wherein the means for averaging comprises one of:
   means for cyclically varying an index of refraction of the multimode optical fiber over a select period of time; and
   means for scrambling a light distribution within the multimode optical fiber.

12. The combustion sensing apparatus of claim 11 wherein the means for averaging comprises one of:
   means for cyclically varying the temperature of the multimode optical fiber; and
   means for cyclically manipulating the multimode optical fiber.

13. The combustion sensing apparatus of claim 12 wherein the means for cyclically manipulating the multimode optical fiber comprises an apparatus configured to perform at least one of:
   twisting the multimode optical fiber;
   stretching the multimode optical fiber;
   shaking the multimode optical fiber.

14. The combustion sensing apparatus of claim 12 wherein the means for cyclically varying the temperature of the multimode optical fiber comprises a thermal element in thermal communication with the multimode optical fiber comprising at least one of a heater, a cooler, a source of fluid heated above ambient temperature and a source of fluid cooled below ambient temperature.

* * * * *